(12) United States Patent
Levine

(10) Patent No.: US 6,525,062 B2
(45) Date of Patent: Feb. 25, 2003

(54) METHOD OF TREATING PAIN USING NALBUPHINE AND OPIOID ANTAGONISTS

(75) Inventor: Jon D. Levine, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/877,669

(22) Filed: Jun. 8, 2001

(65) Prior Publication Data

US 2002/0016331 A1 Feb. 7, 2002

Related U.S. Application Data

(60) Provisional application No. 60/210,367, filed on Jun. 9, 2000.

(51) Int. Cl.$^7$ ............................................... A61K 31/44
(52) U.S. Cl. ....................................................... 514/282
(58) Field of Search ......................................... 514/282

(56) References Cited

U.S. PATENT DOCUMENTS

| | | |
|---|---|---|
| 4,464,378 A | 8/1984 | Hussain |
| 4,573,995 A | 3/1986 | Chen et al. |
| 5,376,662 A | 12/1994 | Ockert |
| 5,473,943 A | 12/1995 | Crain et al. |
| 5,512,578 A | 4/1996 | Crain et al. |
| 5,580,876 A | 12/1996 | Crain et al. |
| 5,750,534 A | 5/1998 | Yoa-Pu et al. |
| 5,767,125 A | 6/1998 | Crain et al. |
| 5,817,665 A | 10/1998 | Dante |
| 5,840,731 A | 11/1998 | Mayer et al. |
| RE36,547 E | 2/2000 | Crain et al. |
| 6,096,756 A | 8/2000 | Crain et al. |
| 6,117,900 A | 9/2000 | Rundfeldt et al. |
| 6,153,621 A | 11/2000 | Hamann |
| 2001/0047005 A1 | 11/2001 | Farrar |

OTHER PUBLICATIONS

Budd, Keith "The use of the opiate antagonist, naloxone, in the treatment of intractable pain" Neuropeptides (edinburgh) (1985), 5 (4–6), 419–22 ISSN: 0143–4179.* de Cazanove, et al. "Determination of Nalbuphine in Human Plasma by High–performance Liquid Chromatography with Electrochemical Detection Application to a Pharmacokinetic Study" *J. of Chromatography B* (1997) vol. 690, pp. 203–210.

Dube, et al. "Determination of Nalbuphine by High–performance Liquid Chromatography with Electrochemical Detection: Application to Clinical Samples from Post–operative Patients" *J. of Chromatography* (1988) vol. 427, pp. 113–120.

Gear, et al. "Action of Naloxone on Gender–dependent Analgesic and Antianalgesic Effects of Nalbuphine in Humans" *J. of Pain* (2000), vol. 1(2), pp. 122–127.

Gear, et al. "The Kappa Opioid Nalbuphine Produces Genger– and Dose–dependent Analgesia and Antianalgesia in Patients with Postoperative Pain" *Pain* (1999) vol. 83, pp. 339–345.

Ho, et al. "Determination of Nalbuphine by High–performance liquid Chromatography with Ultraviolet Detection: Application of Human and Rabbit Pharmacokinetic Studies" *J. of Chromatography B* (1996) vol. 678, pp. 289–269.

Levine, et al. "Potentiation of Pentazocine Analgesia by Low–dose Naloxone" *J. Clin. Invest.* (Nov. 1998) vol. 82, pp. 1574–1577.

Lo, et al. "The Disposition and Bioavailability of Intravenous and Oral Nalbuphine in Healthy Volunteers" *J. Clin. Pharmacol.* (1987) vol. 27, pp. 866–873.

Nicolle, et al. "Rapid and Sensitive High–performance Liquid Chromatographic Assay for Nalbuphine in Plasma" *J. of Chromatography B* (1995) vol. 663, pp. 111–117.

Pao, et al. "High–performance Liquid Chromatographic Method for the Simultaneous Determination of Nalbuphine and its Prodrug, Sebacoyl Dinalburphine Ester, in Dog Plasma and Application to Pharmacokinetic Studies in Dogs"*J. of Chromatography B* (2000) vol. 746, pp. 241–247.

Regents of the University of California, "Finding Could Lead to Morphine Alternative" *Daybreak* http://www.uscf.edu/today/ (2000).

Sung, et al. "Delivery of Nalbuphine and its Prodrugs Across Skin by Passive Diffusion and Iontophoresis" *J. of Controlled Release* (2000) vol. 67, pp. 1–8.

Wetzelsberger, et al. "Internally Standardized Method for the Determination of Nalbuphine in Human Plasma by Means of High Performance Liquid Chromatography with Electrochemical CoulOmetric Detection" *Arzneim–Forsch/Drug Res.* (1988) vol. 38(11), pp. 1768–1771.

Hussain et al., *Pharm. Res.* 5: 615 (1998).
Hussain et al., *Pharm. Res.* 5:113 (1988).
Hussain et al., *J. Pharm. Sci.* 76: 356 (1987).

(List continued on next page.)

Primary Examiner—Theodore J. Criares
Assistant Examiner—Jennifer Kim
(74) Attorney, Agent, or Firm—Townsend and Townsend and Crew LLP

(57) ABSTRACT

Inflammatory or neuropathic pain in both men and women patients is treated by administering, sequentially or simultaneously, (a) nalbuphine and (b) an opioid antagonist selected from naloxone, naltrexone and nalmefene, or a salt or prodrug of nalbuphine and/or the opioid antagonist. Preferably, administration is made of (a) an amount of from about 3 to about 8 mg nalbuphine and (b) from about 0.2 to about 0.8 mg of an opioid antagonist selected from naloxone, naltrexone and nalmefene, or a salt and/or prodrug of either (in an amount that produces in a patient the same blood concentration of the compound in question as would administration of said amount of the nalbuphine or opioid antagonist itself).

Treatment of both inflammatory and neuropathic pain can be achieved; side effects common with $\mu$-opioids such as morphine were not observed.

97 Claims, 10 Drawing Sheets

OTHER PUBLICATIONS

*The Merck Index*, 12th edition, S. Budavari, ed., 1091–1093 (1996).

Rust, L. A. et al.: "Intrathecal narcotics for obstetric analgesia in a community hospital", *American Journal of Obstetrics and Bynecology*, (Jun. 1994) 170 (6) 1643–6; Discussion 1646–8, XP008005676, abstract p. 1644, col. 1.

Lehmann, K.A.: "Opioids: Overview on action, interaction and toxicity", *Supportive Care in Cancer*, (1997) 5/6 (439–444), XP001086567, figure 3, tables 2, 3.

Gerak, L. R. et al.: "Changes in sensitivity to the rate-decreasing effects of opioids in pigeons treated acutely or chronically with nalbuphine", *Behavioural Pharmacology*, (1996) 7/5 (437–447), XP008005675, abstract, col. 1.

Barsan, William G. et al.: "Duration of Antagonistic Effects of Nalmafene and Naloxone in Opiate–Induced Sedation for Emergency Department Procedures", *American Journal of Emergency Medicine*, vol. 7, No. 2 (Mar. 1989).

Konieczko, K. M. et al.: "Antagonism of Morphine–Induced Respiratory Depression with Nalmefene", *British Journal of Anaesthesia*, 61, 318–323 (1988).

France, Charles P. et al.: "Morphine, Saline and Naltrexone Discrimination in Morphine–Treated Pigeons", *The Journal of Pharmacology and Experimental Therapeutics*, vol. 242, No. 1 (1987).

* cited by examiner 2.5 mg Nalbuphine (Nalb)

5 mg Nalbuphine (Nalb)

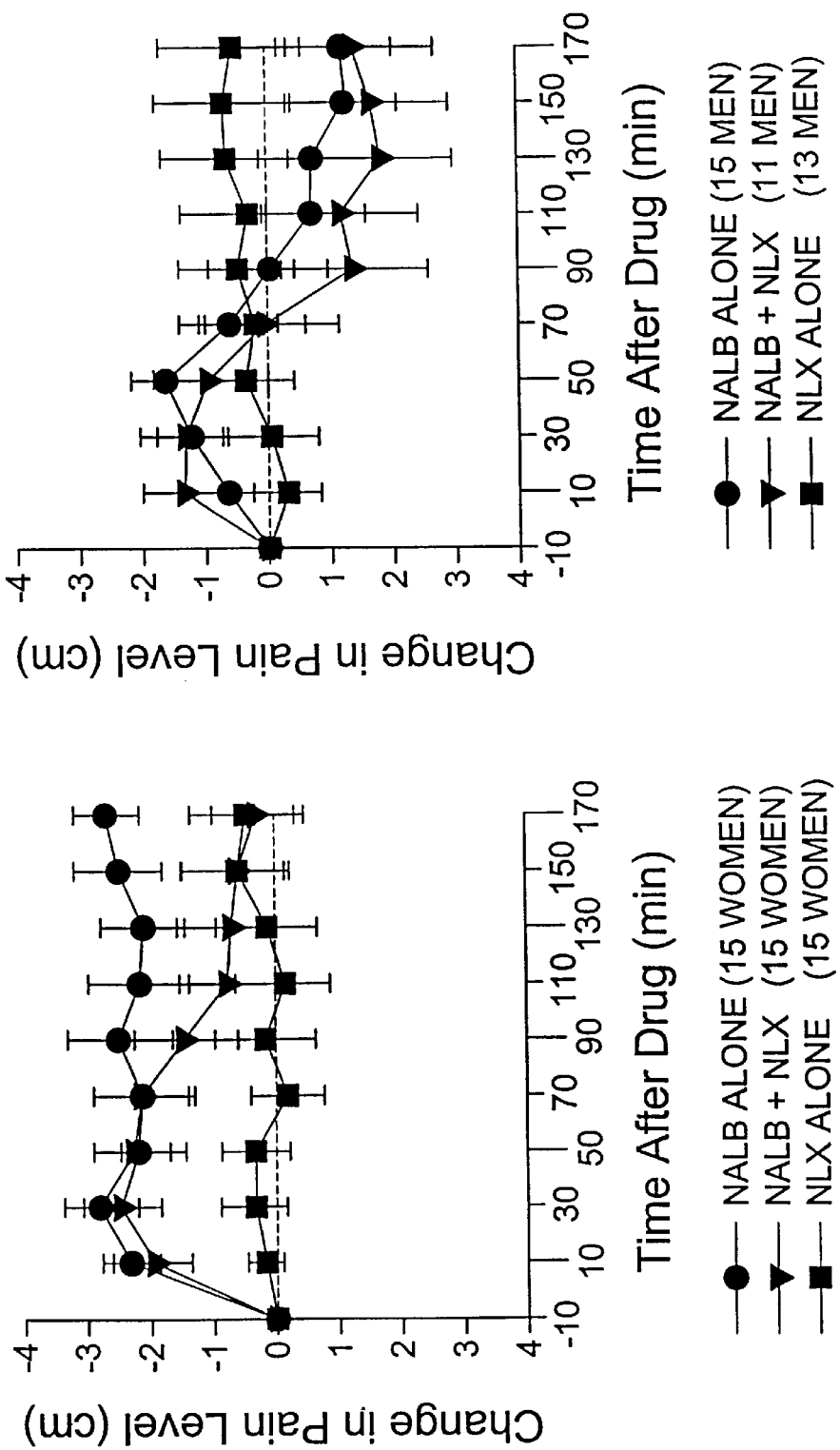

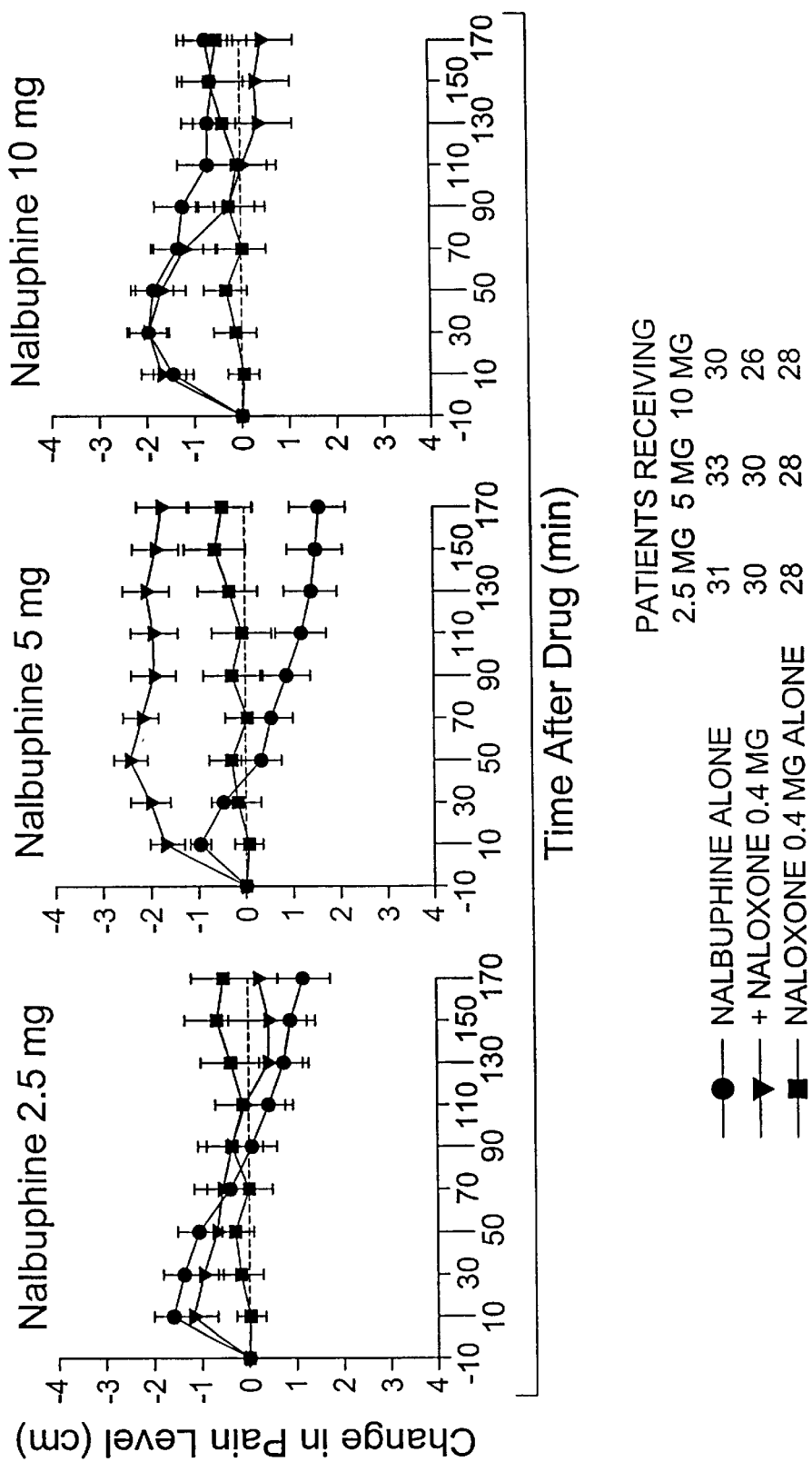

METHOD OF TREATING PAIN USING NALBUPHINE AND OPIOID ANTAGONISTS

STATEMENT AS TO RIGHTS TO INVENTIONS MADE UNDER FEDERALLY SPONSORED RESEARCH AND DEVELOPMENT

This invention was made with government support under Grant No. NR 03923 of the National Institutes of Health. The government has certain rights in this invention.

BACKGROUND OF THE INVENTION

This invention relates to methods and compositions for treating pain in humans using a combination of the kappa-opioid nalbuphine, in a relatively low dosage, with a low dosage of an opioid antagonist selected from naloxone, naltrexone, and nalmefene.

Nalbuphine is a kappa-opioid, a member of the larger opioid group of agonists that includes many well-known agents used to relieve pain. The most well known member of this class is the mu-opioid morphine.

Morphine, of course, is a widely known compound, administered for various purposes, including analgesia. Morphine, in fact, is the compound most often used to treat moderate to severe pain. However, it has known limitations. With time, patients can develop tolerance to it and/or become dependent on it or addicted to it. In addition, morphine can cause severe constipation.

In general, clinical pain conditions can be classified into two categories—traumatic or inflammatory pain, which results from injury to non-neural tissue, for example as occurs after surgery, and in individuals with arthritis, and neuropathic pain, which results from injury to the nervous system. Neuropathic pain, in particular, can be quite severe and not very responsive to narcotic analgesics (see Portenoy, et al., Pain. 43(3): 273–286, 1990. and Hanks, et al., Acta Anaesthesiol. Scand. 1997 Jan; 41(1 Pt. 2): 154–158, 1997). To the knowledge of the inventor, kappa-opioids have not hitherto been tried as a treatment for neuropathic pain, and the use of nalbuphine with an opioid antagonist selected from naloxone, naltrexone, and nalmefene for this purpose in general is new and forms an aspect of this invention.

Levine et al. (1988, J. Clin. Invest. 82(5):1574–77) discloses that, in a study of human patients with postoperative pain after removal of impacted third molars (wisdom teeth), the analgesia produced by administration of 60 mg of the kappa-opioid pentazocine is potentiated by co-administration of a low dose (0.4 mg) of naloxone. The analgesia produced by administration of 8 mg of the mu-opioid morphine is attenuated by co-administration of 0.4 mg of naloxone. Analogous results were obtained in experiments in rats. Levine et al., however, does not disclose administration of a combination of 5 mg of the kappa-opioid nalbuphine with an opioid antagonist such as naloxone. Indeed, Levine et al., does not disclose the administration of a combination comprising nalbuphine in any amount at all.

Crain et al. (U.S. Pat. No. 5,472,943, issued Dec. 5, 1995; U.S. Pat. No. 5,512,578, issued Apr. 30, 1996; U.S. Pat. No. 5,580,876, issued Dec. 3, 1996; U.S. Pat. No. 5,767,125, issued Jun. 16, 1998; U.S. Pat. No. RE. 36,547, reissued Feb. 1, 2000; U.S. Pat. No. 6,096,756, issued Aug. 1, 2000) discloses opiate combinations for enhancing analgesic potency and attenuating dependence liability, in particular, combinations of a bimodally-acting opioid agonist and an excitatory opioid receptor antagonist. According to Crain et al., the bimodally-acting opioid agonist is selected from the group consisting of morphine, codeine, fentanyl analogs, pentazocine, buprenorphine, methadone, enkephalins, dynorphins, endorphins and similarly acting opioid alkaloids and opioid peptides. The excitatory opioid receptor antagonist is selected from the group consisting of naltrexone, naloxone, etorphine, diprenorphine, dihydroetorphine, and similarly acting opioid alkaloids and opioid peptides. Crain et al., however, does not disclose, as a combination for enhancing analgesia, the combination of the kappa-opioid nalbuphine (in any amount, much less 5 mg) and an excitatory opioid antagonist.

Previous studies by the inventor and co-workers determined that nalbuphine's analgesic effects are greater and more consistent in women than in men, suggesting that the pain modulation mechanism activated by nalbuphine is sexually dimorphic (Gear et al., Pain, 83, 339, 1999). In a placebo-controlled dose-response study of human patients with postoperative pain after removal of impacted wisdom teeth, a low dose of nalbuphine (5 mg) did not produce pain modulation effects in women that were any better than those achieved by administration of a dose of placebo. Moreover, administration of a 5 mg dose of nalbuphine in men unexpectedly increased postoperative pain, leading Gear et al. to conclude that in men, the administration of low (5 mg) doses of nalbuphine should be avoided altogether. Gear et al. also does not disclose administration to either women or men of a combination of nalbuphine with an excitatory opioid receptor agonist for pain modulation.

This invention now provides methods and compositions for using the kappa-opioid nalbuphine for treatment of pain of both men and women patients.

BRIEF SUMMARY OF THE INVENTION

According to this invention, it has now been found that administration of a relatively low dosage of nalbuphine can have a dramatic effect on mediation of pain, including both inflammatory and neuropathic pain, when combined with administration (together or sequentially) of a low dosage of an opioid antagonist selected from naloxone, naltrexone, and nalmefene.

In one aspect, the invention comprises a method of treating pain comprising administering to a human in need of such treatment (a) from about 3 to about 8 mg of nalbuphine or a pharmaceutically acceptable salt or prodrug of nalbuphine and (b) from about 0.2 to about 0.8 mg of an opioid antagonist selected from naloxone, naltrexone, and nalmefene, pharmaceutically acceptable salts thereof, and prodrugs therefor, and wherein, if either ingredient is in the form of a salt thereof or a prodrug therefor, said ingredient is present in an amount that, when administered to a patient, produces in the patient the same blood concentration of nalbuphine, or of the narcotic antagonist, as would be produced by administration of from about 3 to about 8 mg of nalbuphine or from about 0.2 to about 0.8 mg of the opioid antagonist, respectively.

In a second aspect, this invention comprises pharmaceutical compositions comprising from about 3 to about 8 mg of nalbuphine or a pharmaceutically acceptable salt or prodrug of nalbuphine and from about 0.2 to about 0.8 mg of an opioid antagonist selected from naloxone, naltrexone, and nalmefene, pharmaceutically acceptable salts thereof, and prodrugs therefor, and wherein, if either ingredient is in the form of a salt thereof or a prodrug therefor, said ingredient is present in an amount that, when administered to a patient, produces in the patient the same blood concentration of nalbuphine, or of the narcotic antagonist, as would administration of from about 3 to about 8 mg of nalbuphine or from about 0.2 to about 0.8 mg of the narcotic antagonist, respectively. These compositions may also comprise one or more pharmaceutically acceptable carriers, such as saline.

In a third aspect, this invention comprises a more concentrated composition that may be used to prepare compositions for administration to patients, namely pharmaceutical compositions comprising (a) nalbuphine, a pharmaceutically acceptable salt of nalbuphine or a prodrug of nalbuphine and (b) an opioid antagonist selected from naloxone, naltrexone, and nalmefene, pharmaceutically acceptable salts thereof, and prodrugs therefor, wherein the weight ratio of ingredient (a) to ingredient (b) is from about 16:1 to about 4:1, and wherein, if either ingredient is in the form of a salt thereof or a prodrug therefor, said ingredient is present in an amount that, when diluted for administration and administered to a patient, produces in the patient the same blood concentration of nalbuphine, or of the narcotic antagonist, as would administration of from about 3 to about 8 mg of nalbuphine or form about 0.2 to about 0.8 mg of the narcotic antagonist, respectively. This composition also may comprise a pharmaceutically acceptable carrier.

Another aspect of this invention, as mentioned above, is the use, in general, of nalbuphine with an opioid antagonist selected from naloxone, naltrexone, and nalmefene, as a treatment for neuropathic pain.

BRIEF DESCRIPTION OF THE DRAWINGS

FIGS. 2 and 3 include data from additional test doses of nalbuphine involving administration of nalbuphine and naloxone to patients having undergone surgery for removal of the third molar ("wisdom") teeth.

DETAILED DESCRIPTION OF THE INVENTION

Figure 1:
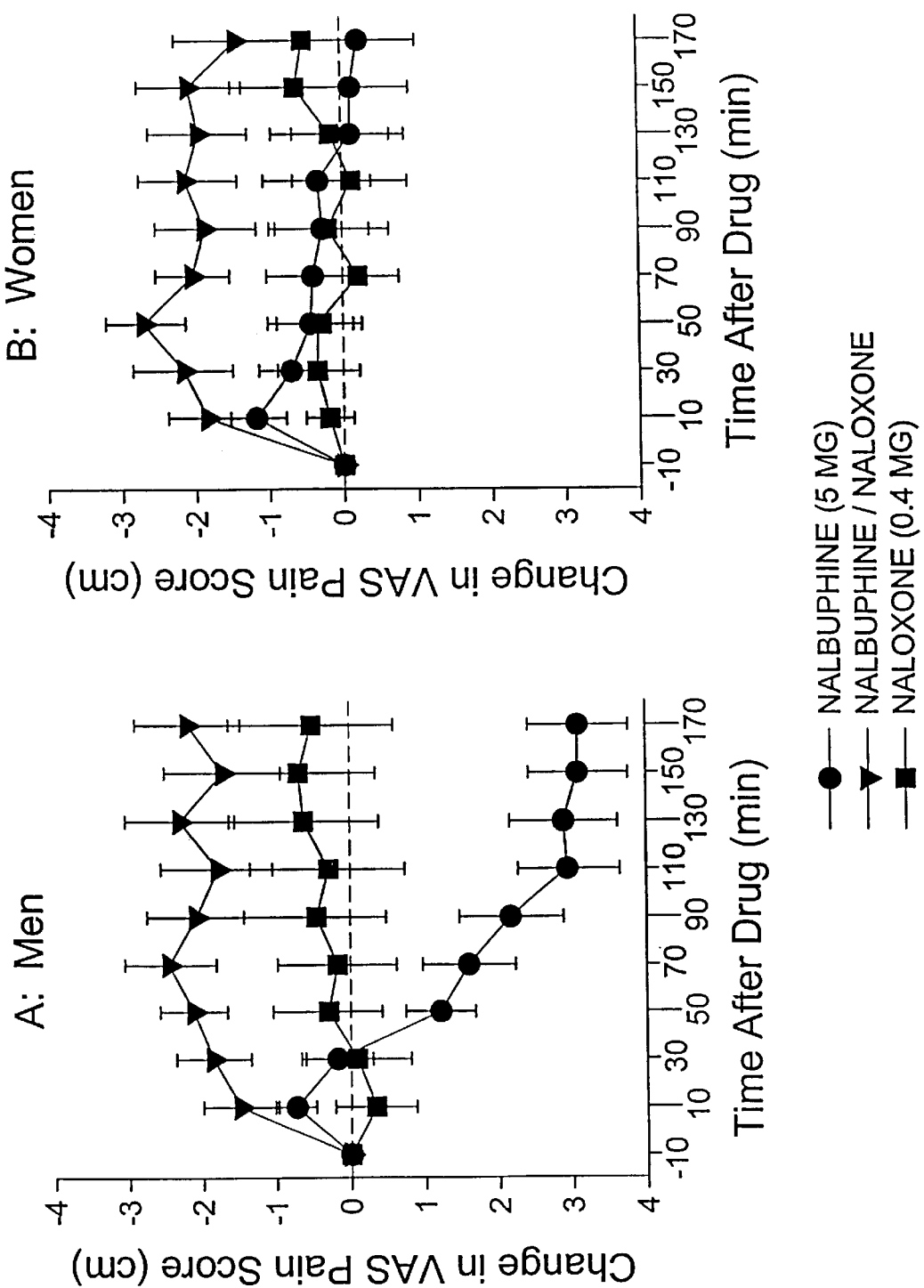
FIG. 1 depicts changes in pain with respect to time after administration of drugs in a first study, showing the effect of the combination of the invention in comparison with administration of nalbuphine or naloxone alone at the same dosages.

This invention involves a method of treating pain that comprises administering to a human in need of such treatment (a) from about 3 to about 8 mg, preferably from about 3.5 to about 7 mg, most preferably about 5 mg, nalbuphine and from about 0.2 mg to about 0.8 mg, preferably about 0.4 mg, of an opioid antagonist selected from naloxone, naltrexone, and nalmefene. The amounts administered thus may comprise about 3, 3.5, 4, 4.5, 5, 5.5, 6, 6.5, 7, 7.5 or 8 mg nalbuphine about 0.2, 0.3, 0.4, 0.5, 0.6, 0.7 or 0.8 mg of the opioid antagonist, respectively (or amounts of salts thereof or prodrug therefor, wherein, if either ingredient is in the form of a salt thereof or a prodrug therefor, said ingredient is present in an amount that, when administered to a patient, produces in the patient the same blood concentration of nalbuphine, or of the opioid antagonist, as would administration of from abut 3 to 8 about mg of nalbuphine or from about 0.2 to about 0.8 mg of the opioid antagonist, respectively).

The invention further comprises pharmaceutical compositions which comprise from about 3 to about 8 mg, preferably from about 3.5 to about 7 mg, most preferably about 5 mg, nalbuphine, or a pharmaceutically acceptable salt or prodrug of nalbuphine (in an amount that, when administered to a patient, produces in the patient the same blood concentration of nalbuphine as administration of from about 3 to about 8 mg of nalbuphine) and from about 0.2 to 0.8 mg, preferably about 4 mg, of an opioid antagonist selected from naloxone, naltrexone and nalmefene (in an amount that, when administered to a patient, produces in the patient the same blood concentration of opioid antagonist as administration of from about 0.2 to about 0.8 mg of the opioid antagonist). The compositions thus may comprise about 3, 3.5, 4, 4.5, 5, 5.5, 6, 6.5, 7, 7.5 or 8 mg nalbuphine in combination with about 0.2, 0.3, 0.4, 0.5, 0.76, 0.7 or 0.8 mg opioid antagonist (or amounts of salts thereof or prodrug therefor, wherein, if either ingredient is in the form of a salt thereof or a prodrug therefor, said ingredient is present in an amount that, when administered to a patient, produces in the patient the same blood concentration of nalbuphine, or of the opioid antagonist, as would administration of from about 3 to about 8 mg of nalbuphine or from about 0.2 to about 0.8 mg of the opioid antagonist, respectively).

The invention further comprises a more concentrated pharmaceutical composition which comprises nalbuphine (or a salt or prodrug of nalbuphine) and an opioid antagonist as mentioned above (or a salt of or prodrug therefor) in which the weight ratio of the nalbuphine to opioid antagonist is from about 16:1 to about 4:1 (or, if a salt or prodrug of either nalbuphine or opioid antagonist is used in such a composition, said ingredient is present in an amount that, when diluted for administration and administered to a patient, produces in the patient the same blood concentration of nalbuphine or of the opioid antagonist as would administration of from about 3 to about 8 mg of nalbuphine or from about 0.2 to about 0.8 mg of the opioid antagonist, respectively). Such a more concentrated composition would be diluted prior to administration to produce a composition that contains the appropriate amounts of nalbuphine and opioid antagonist for administration to the patient. Dilution may take place immediately prior to administration or at any time prior to administration. In the latter case, dilution would be carried out to produce a plurality of single-dosage units to be stored and used for later administration.

The term "about", as used herein, is used to indicate that some departure may be made from the specific amounts stated without departing from the inventive concept. The amount of permissible variation can be up to abut 5% (absolute) from a given amount that is at or near the upper or lower end of the broad ranges, or up to about 20% (absolute) from a given amount that is nearer the center of the ranges.

As with many pharmaceuticals, nalbuphine and the opioid antagonists useable in this invention may be administered either in the form of the free compound or in the form of a pharmaceutically acceptable salt, with a typical salt being a hydrochloride salt. In addition, administration of nalbuphine and/or the opioid antagonists may be performed by administration of a prodrug, that is, a compound that in the body metabolizes or otherwise converts to the active ingredient. Such prodrugs may be, for example, cleavable esters or amines of the active ingredient in question. For example, U.S. Pat. No. 5,750,534 discloses certain alkanoic acid esters of nalbuphine as prodrugs for that compound.

When a prodrug or a pharmaceutically acceptable salt of nalbuphine and/or an opioid antagonist is used for the purposes of this invention, the amount of the salt or prodrug may not necessarily lie within the ranges stated above. The amount of salt or prodrug administered according to this invention is an amount that, when administered to a patient, produces in the patient the same blood concentration of active ingredient, either of nalbuphine or of the opioid antagonist, as the case may be, as would be produced by administration of from about 3 to about 8 mg of nalbuphine or from about 0.2 to about 0.8 mg of the opioid antagonist, respectively.

Any method commonly known in the art may be used to measure the blood concentration. For example, methods for measuring the blood concentration of opioids such as nalbuphine and of opioid antagonists are well-known in the art (see, e.g. Pao et al., 2000, High-performance liquid chromatographic method for the simultaneous determination of nalbuphine and its prodrug, sebacoyl dinalbuphine ester, in dog plasma and application to pharmacokinetic studies in dogs, J. Chromatogr. B Biomed. Sci. Appl. 746(2):241–7; Sung et al., 2000, Delivery of nalbuphine and its prodrugs across skin by passive diffusion and iontophoresis, J. Control. Release 67(1):1–8; de Cazanove et al., 1997, Determination of nalbuphine in human plasma by high-performance liquid chromatography with electrochemical detection. Application to a pharmacokinetic study, J. Chromatogr. B Biomed. Sci. Appl. 690(1–2):203–10; Ho et al., 1996, Determination of nalbuphine by high-performance liquid chromatography with ultraviolet detection: application to human and rabbit pharmacokinetic studies, J. Chromatogr. B Biomed. Appl. Apr. 12, 1996; 678(2):289–96; Nicolle et al., 1995, Rapid and sensitive high-performance liquid chromatographic assay for nalbuphine in plasma, J. Chromatogr. B Biomed. Appl. Jan. 6, 1995;663(1):111–7; Wetzelsberger et al., 1988, Internally standardized method for the determination of nalbuphine in human plasma by means of high performance liquid chromatography with electrochemical coulometric detection, Arzneimittelforschung December 1988; 38(12):1768–71; Dube et al., 1988, Determination of nalbuphine by high-performance liquid chromatography with electrochemical detection: application to clinical samples from postoperative patients, J. Chromatogr. May 13, 1988;427(1):113–20; Lo et al., 1987, The disposition and bioavailability of intravenous and oral nalbuphine in healthy volunteers, J. Clin. Pharmacol. Nov. 27, 1987(11):866–73; incorporated herein by reference in their entireties).

In the case of a hydrochloride salt, the weight of hydrochloride as compared to the weight of the active molecule is relatively small, so that a hydrochloride salt will be used in an amount approximately the same as that of the active ingredient. However, in the case of a prodrug having a large cleavable group, for example $C_{20}$ alkanoic acid derivatives of nalbuphine (as mentioned in U.S. Pat. No. 5,750,534), the prodrug may have a substantially higher molecular weight than the active ingredient alone, so that the amount of prodrug used could be substantially greater than that of the active ingredient itself, to produce the same blood concentration of active ingredient in the patient's body.

Nalbuphine and the opioid antagonist respectively are preferably administered simultaneously, but can be administered sequentially, in either order. Sequential administration is carried out within a time period such that the opioid antagonist can modulate the effects of nalbuphine. Preferably, one compound, e.g., nalbuphine, is administered within 6 to 8 hours of administration of the other compound, e.g., the opioid antagonist. Also preferably, administration of one compound is within 2 hours of administration of the other compound, more preferably within 10 to 15 minutes, and most preferably, at substantially the same time. They preferably are administered using the same route of administration, but this is not necessary. Thus, if compositions of nalbuphine and the opioid antagonist are available which are not generally administered in the same route, they may be administered by different routes. For example, nalbuphine and the opioid antagonist may be administered together via intramuscular injection or intravenously, or one compound may be administered by intramuscular injection and the other intravenously. Other routes of administration, for example oral or parenteral (intravenous, intramuscular or subcutaneous injection) may be used, as well as direct injection to the central nervous system (intrathecally).

When the compositions of the invention are used to treat neuropathic pain or chronic pain, they are preferably formulated for oral administration, and most preferably, are formulated for time-released oral administration. When the compositions of the invention are used to treat acute inflammatory pain, they are preferably formulated for intravenous, e.g., parenteral, administration. When the compositions of the invention are used to treat chronic inflammatory pain, they are preferably formulated for oral administration.

For parenteral administration, the compounds are best used in the form of a sterile aqueous solution that may also contain other dissolved substances such as preservatives, stabilizers, and pH adjusting agents.

Nalbuphine and the opioid antagonist may be administered by obtaining commercially available products containing these individual components and combining them when the administration is to be carried out, or administering them separately, as described above. Alternatively, compositions may be prepared containing combinations of nalbuphine with the opioid antagonists (or salts or prodrugs of either or both), and the combination administered as a single composition. Such combined compositions may be liquid or solid, and are prepared in a conventional manner by the addition of suitable pharmaceutically acceptable ingredients including carriers, fillers, diluents, lubricants, preservatives, and the like. Solid forms include tablets, capsules, granules and powders. Liquid forms include solutions, suspensions and emulsions.

Compositions containing nalbuphine and an opioid antagonist according to this invention may be prepared in unit dosage forms or in a more concentrated form that may be diluted at the point of administration.

In prior work, it had been shown that nalbuphine, when administered at a low dose of 5 mg to treat postoperative pain after extraction of impacted molars, produced a marked increase in pain in men while in women the effect of this dose was similar to a placebo. It was, thus, surprising that administration of a relatively low dose of nalbuphine and an opioid antagonist, such as naloxone, at an even lower dose could produce marked relief from pain after such an operation.

This result is particularly surprising in the treatment of neuropathic pain. In general, there is widespread perception among clinicians that kappa-opioids are less effective analgesics than $\mu$-opioids such as morphine, although they have been shown to be effective for painful, peripheral neuropathy in experimental animal models. Medical management of painful peripheral neuropathies presents a true therapeutic challenge. In the oral cavity neuropathic pain can result from injection of local anesthetics. Trigeminal neuropathic pain, like other painful peripheral neuropathies, is generally poorly responsive to currently available therapies. Agents that might have some limited effect on pain associated with neuropathy include tricyclic antidepressants, antiepileptics, neurontin and $\mu$-opioids. The $\mu$-opioids suffer from significant side effects including mental confusion, constipation and respiratory depression, which further limit their efficacy.

It was thus quite surprising that the combination of nalbuphine and an opioid antagonist according to this invention proved efficacious for treating neuropathic pain. The co-administration of these two ingredients in the dosages described above can produce effective pain relief and at the same time avoid side effects that are associated with $\mu$-opioid analgesics including dysphoria and the potential for addiction or dependency. For treatment of neuropathic pain, preferably the amount of opioid antagonist administered to the patient is at least 10–15-fold less than the amount of nalbuphine administered.

The following examples further illustrate this invention.

Results of these examples are reported using a visual analog scale (VAS). This is a subjective measurement of pain, in which persons participating in the study are requested to indicate a level of pain at a certain time on a 10-cm line. The patient makes an indication on the line at a value from 0 to 10 indicating the level of pain felt at that time (where 0 indicates no pain and 10 indicates the worst pain imaginable to the patient). Patients rated pain on the VAS at 20-minute intervals, both before and after administration of the active agents according to this invention. Tabulations were then made indicating increase or decrease in the pain level with time, with a negative value indicating a decrease in pain experienced by the patient and a positive value, an increase in such pain.

EXAMPLE 1

In this clinical trial, 88 patients underwent standardized surgery by the same oral surgeon for removal of third molar ("wisdom") teeth, including at least one bony impacted mandibular third molar. Prior to surgery, patients received intravenous diazepam, nitrous oxide, and a local anesthetic (mepivacaine without vasoconstrictor to obtain a nerve block of short duration). After surgery, each patient was randomly assigned to receive, in an open injection, double-blinded fashion, through an intravenous line, an injection of either naloxone (0.4 mg) or a mixture of this dose of naloxone and nalbuphine (5 mg; Abbott Laboratories, Abbott Park, Ill.).

An earlier study (Gear, et al., Pain, 83, 339, 1999) had demonstrated a pain-enhancing effect of 5 mg of nalbuphine in men. Therefore, nalbuphine was not administered alone at that dosage to men in this evaluation. Instead, data from that previous study for 33 of the 88 patients (i.e., those who received nalbuphine alone) were included in the current study, to avoid replication of an experimental protocol that resulted in enhanced pain. The previous and current studies were performed sequentially in the same facility under identical conditions with the same surgical and experimental protocols, and the same oral surgeon and research personnel who were blinded to the experimental treatments in all cases, so it is felt that the use of data obtained from the previous study rather than repeating a pain-causing procedure had little or no effect on the results. Most of the data from both studies were collected within a single eight-month period. Therefore, the observed differences between the groups of patients are probably not due to the use of the data from the previous study.

Criteria for administration of the test drug were an elapse of a period of at least 80 minutes after the onset of the local anesthetic and a pain rating that was greater than one quarter (2.5 cm) of the maximum possible visual analog scale (VAS) rating (10 cm). Baseline pain intensity was defined as the last VAS pain rating before administration of the test drug or drugs. VAS pain ratings were recorded at 20-minute intervals beginning ten minutes after administration of the test drug. The duration of the experiment, measured from the time of administration of the test drug, was three hours. For each patient, the magnitude of the analgesic response was defined as the difference between the pain rating at each time point following test drug administration and the baseline VAS pain rating.

FIG. 1 depicts the results of this study, namely the effect on postoperative pain of nalbuphine (5 mg), naloxone (0.4 mg), and a combination of nalbuphine and naloxone (5 mg+0.4 mg), plotted as changes in postoperative pain level over the 3 hours following administration. "Change in VAS pain score" (ordinate), recorded on a 10 cm visual analog scale (VAS), represents changes from the baseline level (represented by the horizontal dashed lines) after various times. Decreased pain scores (i.e., analgesia) are above the baseline. Data are plotted as mean+sem (standard error of the mean).

The responses of men who received nalbuphine, naloxone, or nalbuphine combined with naloxone are shown in FIG. 1A. The responses of women who received nalbuphine, naloxone, or nalbuphine combined with naloxone are depicted in FIG. 1B.

Analyses of variance (ANOVA) were conducted. These analyses failed to demonstrate either significant main effects or interaction effects for either naloxone alone or the nalbuphine/naloxone combination, indicating a lack of gender differences in response to either treatment. However, a significant gender x treatment interaction was found with nalbuphine alone, as reported in our previous study.

EXAMPLE 2

Figure 2A:
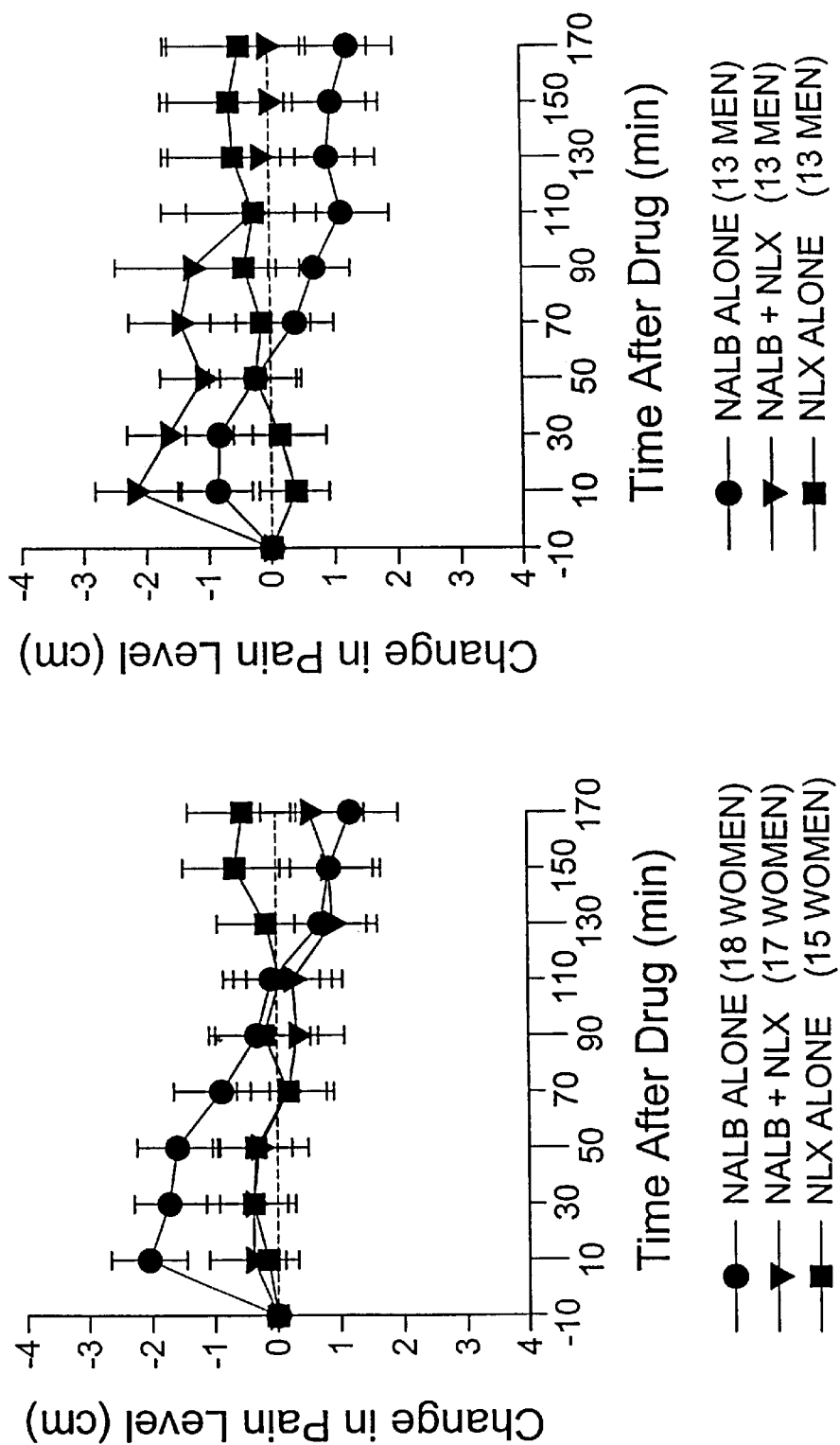
Figure 2B:
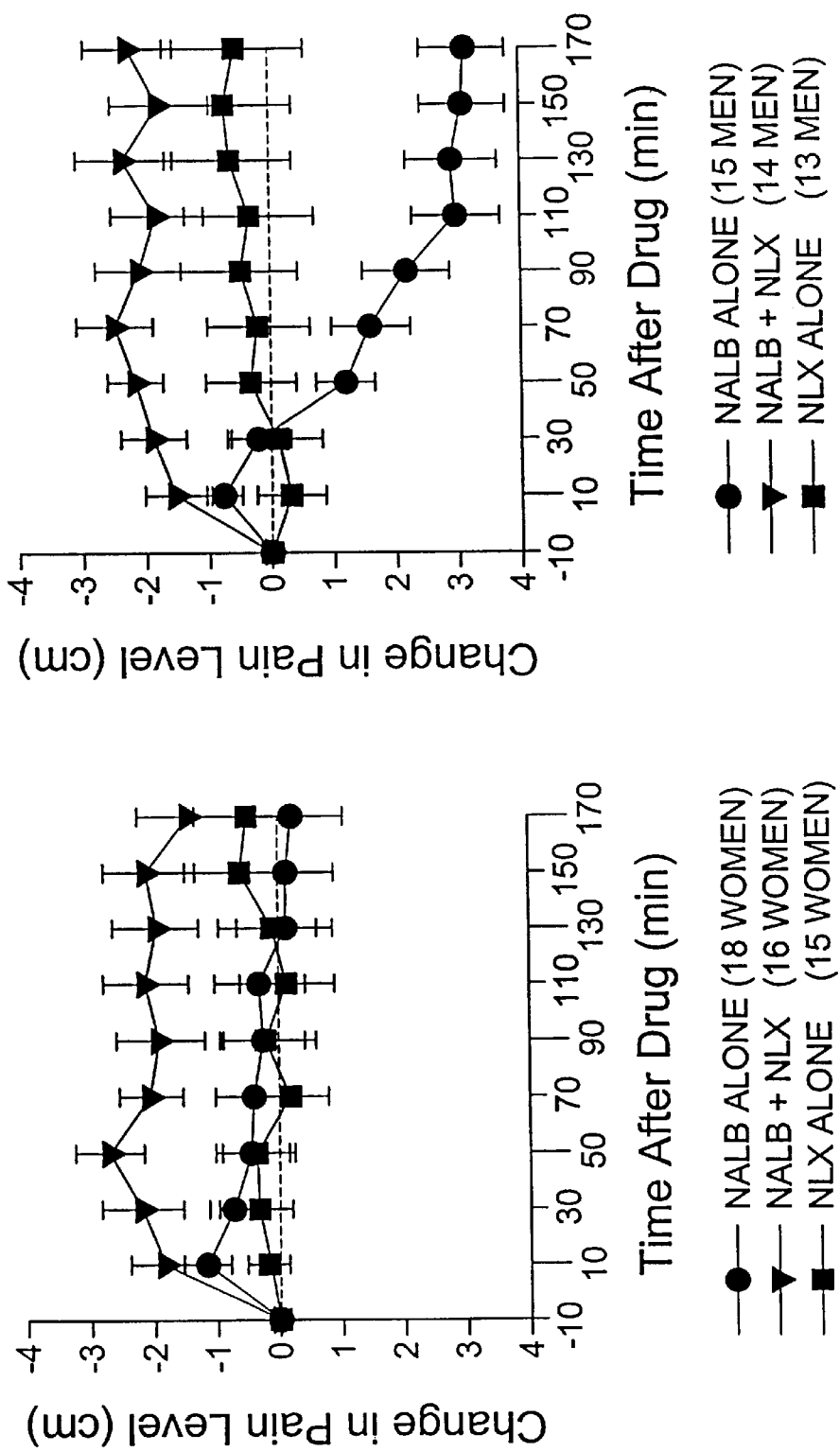

FIGS. 2 and 3 show results of continuations of the experiments described in Example 1, with additional patients and with administration of nalbuphine at higher (10 mg) and lower (2.5 mg) doses, alone. FIG. 2 shows separate results for women and men patients and FIG. 3 shows the combined results for both.

As can be seen from FIG. 2, nalbuphine alone at 2.5 mg initially produced slightly better pain relief in women than either naloxone at 0.4 mg or the combination of nalbuphine (at 2.5 mg) plus naloxone at 0.4 mg. However, thereafter, the combination of nalbuphine and naloxone produced relief from pain substantially the same as nalbuphine alone, and with less effect than naloxone alone. In men, nalbuphine at 2.5 mg plus naloxone at 0.4 mg initially produced somewhat better relief than either naloxone alone or nalbuphine alone, but this effect was not maintained (the data for nalbuphine alone, as mentioned previously, was taken from a previous study).

At a combination of nalbuphine 5 mg plus naloxone 0.4 mg, the combination was substantially better than either nalbuphine alone or naloxone alone at the same levels, for both women and men patients. This is not only surprising in general but is particularly surprising for men patients since, as shown in the chart, the previous study showed that the 5 mg level of nalbuphine had produced an increase in pain.

At a higher level of 10 mg nalbuphine, the combination produced results approximately equivalent to a dose of 10 mg nalbuphine alone for the first 70 minutes or so. Thereafter the combination produced less relief from pain than nalbuphine alone at that level in women, and less than naloxone alone at 0.4 mg in men.

FIG. 3 also shows comparative results of 2.5, 5, and 10 mg nalbuphine respectively in combination with 0.4 mg naloxone.

EXAMPLE 3

Figure 4:
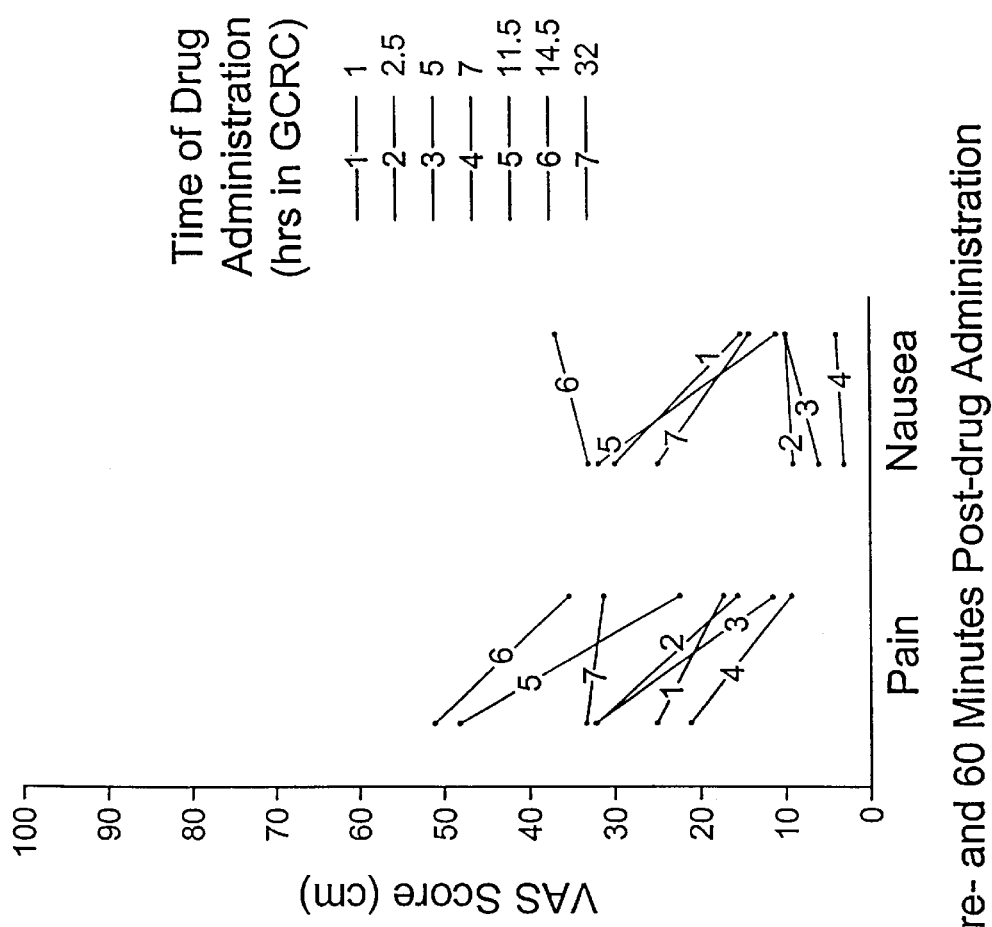
FIGS. 4–6 represent individual data showing the effect of a combination of nalbuphine (5 mg) and naloxone (0.4 mg) according to this invention used to treat pain resulting from LeFort I osteotomy with multiple administration.
Figure 5:
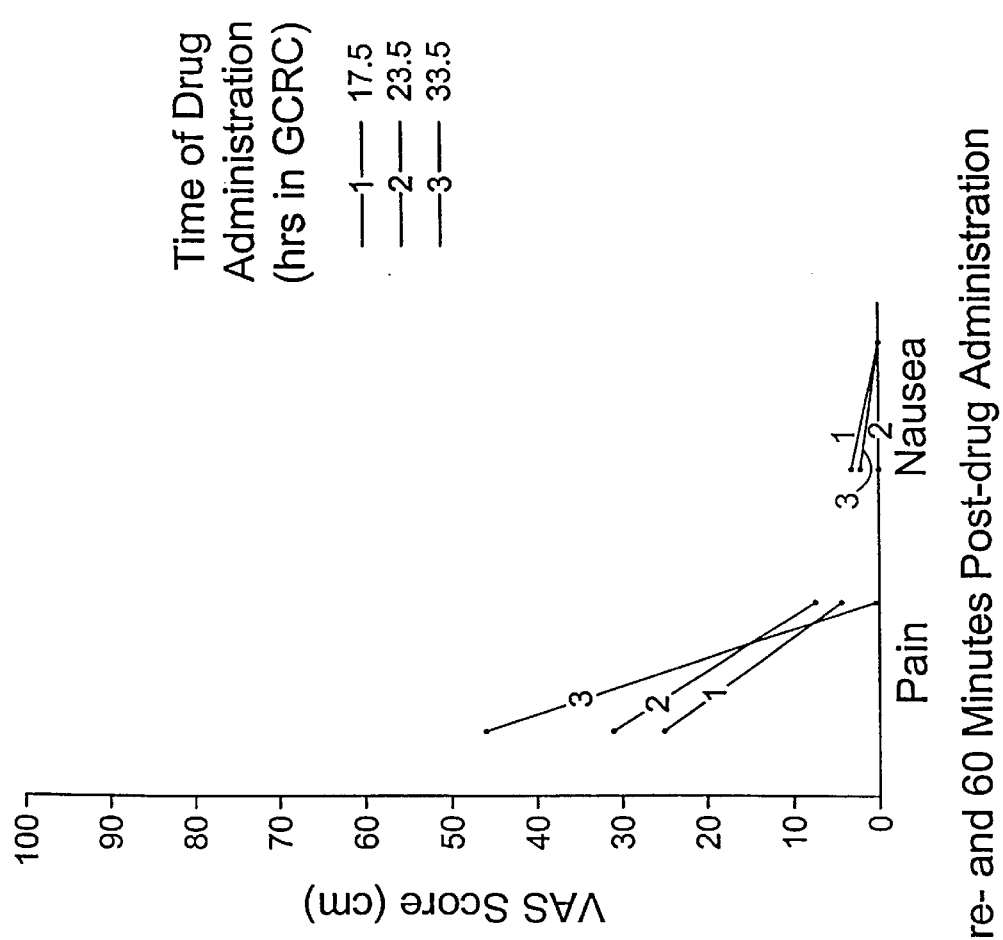
Figure 6:
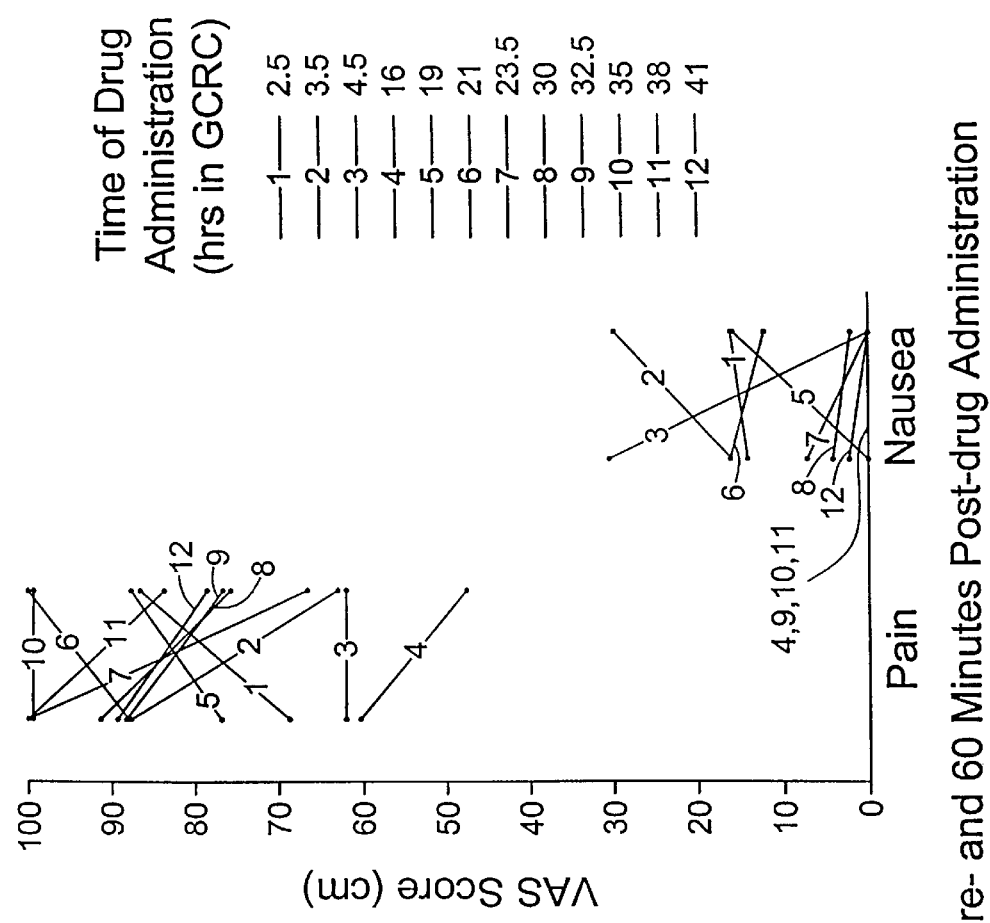

This example describes the treatment of postoperative pain following Le Fort I osteotomy using intravenous administration of a combination of nalbuphine and naloxone. In all three patients, repeated administration produced marked analgesia. While a single administration of nalbuphine (5 mg) plus naloxone (0.4 mg) produces powerful and long-lasting analgesia in both males and females (examples 1 and 2, above), this analgesic could have even greater clinical impact if the efficacy were sustained during repeated administration. In a preliminary study in 3 patients who underwent a Le Fort I osteotomy surgical procedure, 5 mg nalbuphine plus 0.4 mg naloxone were administered when requested by the patient. The VAS pain scores just prior to administration of the drug combination and 60 minutes afterwards are recorded in FIGS. 4, 5 and 6. The same data for the major side-effect, nausea, for these three patients, are also presented. The left end of the line represents the visual analog scale (pain and nausea) rating immediately before drug administration; the right side represents the visual analog scale rating 60 minutes after administration. As can be seen, most of the lines descend to the right, indicating that nausea as well as pain decreased following multiple administrations. Thus, three patients had repeated effective analgesia following most drug administrations over a 48-hour period, with, if anything a decrease in nausea associated with each administration. This study further suggests that early tolerance to the nalbuphine plus naloxone combination does not occur.

EXAMPLE 4

(Treatment of Neuropathic Pain)

Figure 7:
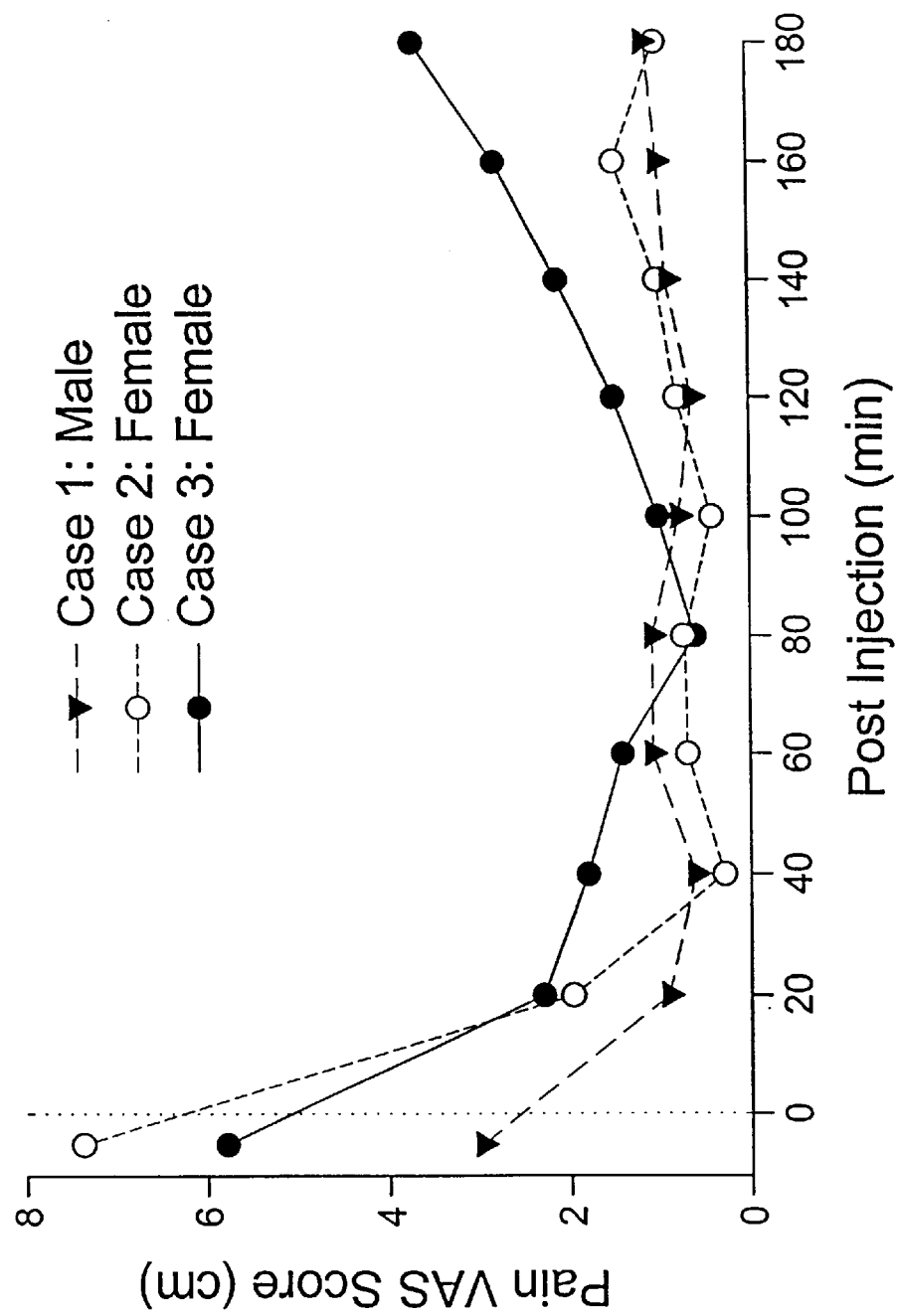
FIG. 7 depicts results for individual patients of a combination of nalbuphine and naloxone according to this invention, used to treat pain resulting from injury to the lingual nerve.
Figure 8:
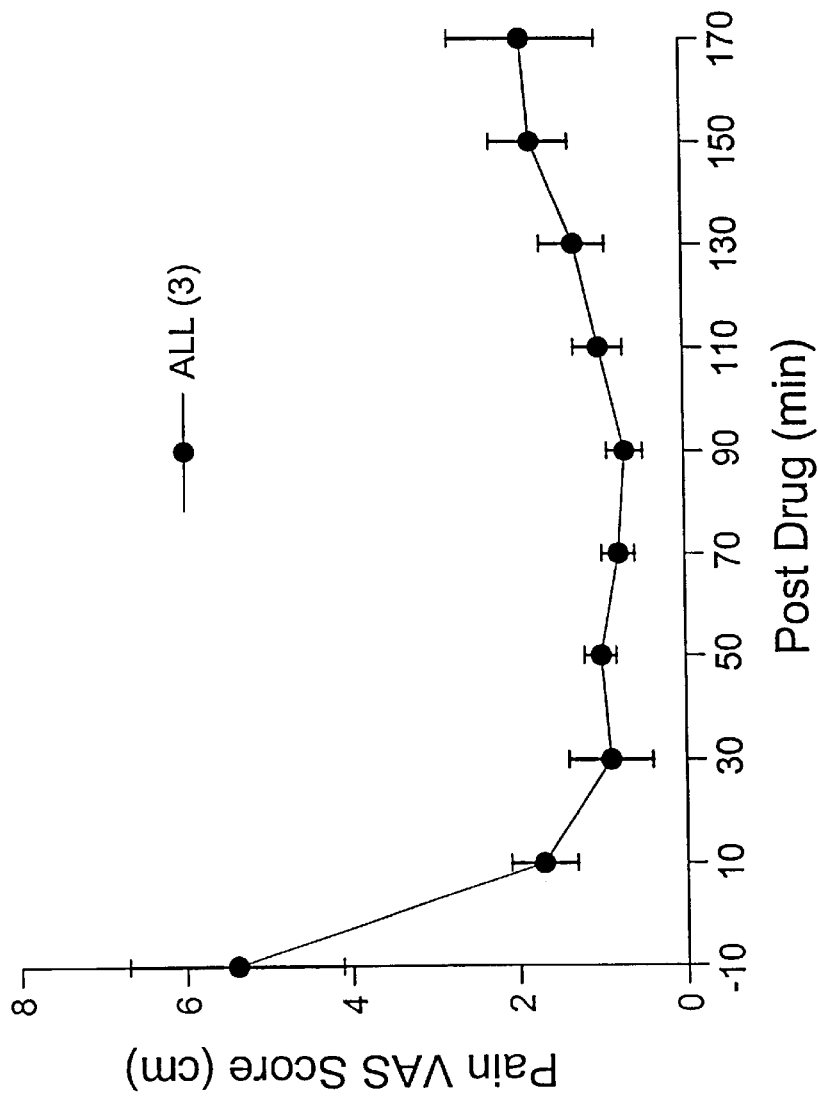
FIG. 8 is a composite of the results for the three patients for whom individual data is shown in FIG. 7.

This example describes the treatment of medically refractory trigeminal neuropathy in three patients using intravenous administration of a combination of nalbuphine and naloxone. Painful peripheral neuropathies are frequent complications of chemical and mechanical injuries and metabolic disorders, and are relatively refractory to narcotic analgesics. It has been documented that inferior alveolar nerve block can cause painful peripheral neuropathy. In this example, medically refractory painful trigeminal neuropathy in three patients was treated with intravenous administration of a combination of nalbuphine (5 mg) and naloxone (0.4 mg). In all patients this combination produced marked analgesia (FIGS. 7 and 8). These findings suggest a novel form of medical management for chronic neuropathic pain. This is extremely important since neuropathic pain is poorly managed by available therapies.

In all three patients this combination produced marked analgesia. This result is believed to represent the first showing of effective treatment of neuropathic pain with a kappa-opioid.

The study involved three patients with painful peripheral neuropathy involving the mandibular division of the trigeminal nerve. One was a 42-year-old man, the second a 40-year-old woman, and the third a 25-year-old woman. Each patient discontinued all medications that had been prescribed to treat pain 2 weeks prior to the test date. They had reported that those medications had little effect.

The test ingredients were administered via an intravenous catheter. Pain intensity was measured using a 10 cm VAS with the words "no pain" at the extreme left and the words "worst pain imaginable" at the extreme right. FIG. 7 shows the level of pain (on the VAS scale) experienced by each of the three patients individually at times up to about 180 minutes after injection. FIG. 8 is a composite for all three patients, showing the relative change in pain in the same approximate time period. Extremely marked analgesia was achieved for at least a 2.5-hour period.

It should be noted that this invention is not limited to the specific materials, test procedures, methods of administration and the like, described herein, but is to be regarded as indicated only by the claims that follow.

What is claimed is:

1. A method of treating pain comprising administering to a human patient in need of such treatment synergistically effective amounts of (a) from about 3 to about 8 mg of nalbuphine, or an amount of a pharmaceutically acceptable salt or prodrug of nalbuphine that produces in the human patient the same blood concentration of nalbuphine as would administration of from about 3 to 8 mg of nalbuphine, and (b) from about 0.2 to about 0.8 mg of an opioid antagonist selected from the group consisting of naloxone, naltrexone, nalmefene, or an amount of a pharmaceutically acceptable salt or prodrug of the opioid antagonist that produces in the human patient the same blood concentration of opioid antagonist as would administration of from about 0.2 to 0.8 mg of said opioid antagonist.

2. The method of claim 1 in which from about 3.5 to about 7 mg of nalbuphine is administered, or said nalbuphine salt or prodrug is administered in an amount that produces in the human patient the same blood concentration of nalbuphine as would administration of from about 3.5 to about 7 mg of nalbuphine.

3. The method of claim 1 in which about 5 mg of nalbuphine is administered, or said nalbuphine salt or prodrug is administered in an amount that produces in the human patient the same blood concentration of nalbuphine as would administration of about 5 mg of nalbuphine.

4. The method of claim 1 in which about 0.4 mg of the opioid antagonist is administered, or said opioid antagonist salt or prodrug is administered in an amount that produces in the human patient the same blood concentration of the opioid antagonist as would administration of about 0.4 mg of the opioid antagonist.

5. The method of claim 2 in which about 0.4 mg of the opioid antagonist is administered, or said opioid antagonist salt or prodrug is administered in an amount that produces in the human patient the same blood concentration of the opioid antagonist as would administration of about 0.4 mg of the opioid antagonist.

6. The method of claim 3 in which about 0.4 mg of the opioid antagonist is administered, or said opioid antagonist salt or prodrug is administered in an amount that produces in the human patient the same blood concentration of the opioid antagonist as would administration of about 0.4 mg of the opioid antagonist.

7. The method of claim 1 in which the opioid antagonist comprises naloxone, a pharmaceutically acceptable salt thereof or a prodrug therefor.

8. The method of claim 2 in which the opioid antagonist comprises naloxone, a pharmaceutically acceptable salt thereof or a prodrug therefor.

9. The method of claim 3 in which the opioid antagonist comprises naloxone, a pharmaceutically acceptable salt thereof or a prodrug therefor.

10. The method of claim 4 in which the opioid antagonist comprises naloxone, a pharmaceutically acceptable salt thereof or a prodrug therefor.

11. The method of claim 5 in which the opioid antagonist comprises naloxone, a pharmaceutically acceptable salt thereof or a prodrug therefor, the method of claim 1 wherein the pain comprises inflammatory pain.

12. The method of claim 6 in which the opioid antagonist comprises naloxone, a pharmaceutically acceptable salt thereof or a prodrug therefor.

13. The method of claim 1 wherein the pain comprises inflammatory pain.

14. The method of claim 1 in which the nalbuphine and opioid antagonist, and/or salts or prodrugs of either, are administered within eight hours of one another.

15. The method of claim 1 in which the nalbuphine and opioid antagonist, and/or salts or prodrugs of either, are administered within two hours of one another.

16. The method of claim 1 in which the nalbuphine and opioid antagonist, and/or salts or prodrugs of either, are administered within 15 minutes of one another.

17. The method of claim 1 in which the nalbuphine and opioid antagonist, and/or salts or prodrugs of either, are administered together at substantially the same time.

18. The method of claim 1 comprising sequential administration of nalbuphine and the opioid antagonist, and/or salts or prodrugs of either.

19. The method of claim 1 comprising parenteral administration of at least one of the nalbuphine and opioid antagonist, and/or salts or prodrugs of either.

20. The method of claim 1 comprising intravenous administration of at least one of the nalbuphine and opioid antagonist, and/or salts or prodrugs of either.

21. A method of treating neuropathic pain comprising administering to a human patient in need of such treatment synergistically effective amounts of (a) nalbuphine, or a pharmaceutically acceptable salt or prodrug of nalbuphine, and (b) an opioid antagonist, a prodrug thereof, or a pharmaceutically acceptable salt thereof, wherein the opioid antagonist is selected from the group consisting of naloxone, naltrexone and nalmefene.

22. The method of claim 21 in which the opioid antagonist comprises naloxone, a pharmaceutically acceptable salt thereof or a prodrug therefor.

23. The method of claim 21 wherein the amount of said opioid antagonist administered is 10–15-fold less than the amount of the nalbuphine administered.

24. The method of claim 1 in which from about 3 to about 8 mg of nalbuphine is administered, and the opioid antagonist is selected from the group consisting of naloxone, naltrexone, and nalmefene.

25. The method of claim 24 in which from about 3.5 to about 7 mg of nalbuphine is administered.

26. The method of claim 24 in which about 5 mg of nalbuphine is administered.

27. The method of claim 24 in which about 0.4 mg of the opioid antagonist is administered.

28. The method of claim 25 in which about 0.4 mg of the opioid antagonist is administered.

29. The method of claim 26 in which about 0.4 mg of the opioid antagonist is administered.

30. The method of claim 24 in which the opioid antagonist comprises naloxone.

31. The method of claim 25 in which the opioid antagonist comprises naloxone.

32. The method of claim 26 in which the opioid antagonist comprises naloxone.

33. The method of claim 32 in which about 0.4 mg of naloxone is administered.

34. The method of claim 24 wherein the pain comprises inflammatory pain.

35. The method of claim 24 wherein the pain comprises neuropathic pain.

36. The method of claim 24 in which the nalbuphine and opioid antagonist are administered within eight hours of one another.

37. The method of claim 24 in which the nalbuphine and opioid antagonist are administered within two hours of one another.

38. The method of claim 24 in which the nalbuphine and opioid antagonist are administered within 15 minutes of one another.

39. The method of claim 24 in which the nalbuphine and opioid antagonist are administered together at substantially the same time.

40. The method of claim 24 comprising sequential administering of nalbuphine and the opioid antagonist.

41. The method of claim 24 comprising parenteral administering of at least one of the nalbuphine and opioid antagonist.

42. The method of claim 24 comprising intravenous administering of at least one of the nalbuphine and opioid antagonist.

43. The method of claim 33 in which the nalbuphine and opioid antagonist are administered within 15 minutes of one another.

44. The method of claim 33 in which the nalbuphine and opioid antagonist are administered together at substantially the same time.

45. A method of treating pain comprising administering to a human patient in need of such treatment synergistically effective amounts of (a) nalbuphine or a pharmaceutically acceptable salt or prodrug of nalbuphine; and (b) an opioid antagonist selected from the group consisting of naloxone, naltrexone, and nalmefene, and pharmaceutically acceptable prodrugs and salts of said opioid antagonists, wherein the amount of said opioid antagonist administered is 10–15-fold less than the amount of the nalbuphine administered, and wherein, if either ingredient is in the form of a prodrug or a salt thereof, said ingredient is present in an amount that produces, when administered to a human patient the same blood concentration of nalbuphine or said opioid antagonist as would administration of nalbuphine or said opioid antagonist, respectively.

46. The method of claim 45 in which the amount of said opioid antagonist administered is 12.5-fold less than the amount of the nalbuphine administered.

47. The method of claim 45 or 46 in which ingredient (a) is nalbuphine.

48. The method of claim 45 or 46 in which ingredient (b) is naloxone.

49. The method of claim 45 or 46 which ingredient (b) is naltrexone.

50. The method of claim 45 or 46 in which ingredient (b) is nalmefene.

51. The method of claim 45 or 46 in which the pain comprises inflammatory pain.

52. The method of claim 45 or 46 in which the pain comprises neuropathic pain.

53. The method of claim 45 or 46 in which ingredient (a) and ingredient (b) are administered within eight hours of one another.

54. The method of claim 45 or 46 in which ingredient (a) and ingredient (b) are administered within two hours of one another.

55. The method of claim 45 or 46 in which ingredient (a) and ingredient (b) are administered within 15 minutes of one another.

56. The method of claim 45 or 46 in which ingredient (a) and ingredient (b) are administered at substantially the same time.

57. The method of claim 45 or 46 comprising sequential administering of ingredient (a) and ingredient (b).

58. The method of claim 45 or 46 comprising parenteral administering of at least one of ingredient (a) and ingredient (b).

59. The method of claim 45 or 46 comprising intravenous administering of at least one of ingredient (a) and ingredient (b).

60. The method of claim 59 in which ingredient (a) and ingredient (b) are administered within 15 minutes of one another.

61. The method of claim 60 in which ingredient (a) and ingredient (b) are administered at substantially the same time.

62. The method of claim 47 in which ingredient (b) is naloxone.

63. The method of claim 47 in which ingredient (b) is naltrexone.

64. The method of claim 47 in which ingredient (b) is nalmefene.

65. The method of claim 47 in which the pain comprises inflammatory pain.

66. The method of claim 47 in which the pain comprises neuropathic pain.

67. The method of claim 47 in which ingredient (a) and ingredient (b) are administered within eight hours of one another.

68. The method of claim 47 in which ingredient (a) and ingredient (b) are administered within two hours of one another.

69. The method of claim 47 in which ingredient (a) and ingredient (b) are administered within 15 minutes of one another.

70. The method of claim 47 in which ingredient (a) and ingredient (b) are administered at substantially the same time.

71. The method of claim 47 comprising sequential administration of ingredient (a) and ingredient (b).

72. The method of claim 47 comprising parenteral administration of at least one of ingredient (a) and ingredient (b).

73. The method of claim 47 comprising intravenous administration of at least one of ingredient (a) and ingredient (b).

74. The method of claim 73 in which ingredient (a) and ingredient (b) are administered within 15 minutes of one another.

75. The method of claim 74 in which ingredient (a) and ingredient (b) are administered at substantially the same time.

76. A method of treating pain comprising administering to a human patient in need of such treatment synergistically effective amounts of (a) nalbuphine, or a pharmaceutically acceptable salt or prodrug of nalbuphine; and (b) an opioid antagonist, a prodrug thereof, or a pharmaceutically acceptable salt thereof, wherein the opioid antagonist is selected from the group consisting of naloxone, naltrexone and nalmefene.

77. The method of claim 76 in which from about 3 to about 8 mg of nalbuphine is administered, or said nalbuphine salt or prodrug is administered in an amount that produces in the human patient the same blood concentration of nalbuphine as would administration of from about 3 to about 8 mg of nalbuphine.

78. The method of claim 76 in which about 0.4 mg of the opioid antagonist is administered, or said opioid antagonist salt or prodrug is administered in an amount that produces in the human patient the same blood concentration of the opioid antagonist as would administration of about 0.4 mg of the opioid antagonist.

79. The method of claim 77 in which about 0.4 mg of the opioid antagonist is administered, or said opioid antagonist salt or prodrug is administered in an amount that produces in the human patient the same blood concentration of the opioid antagonist as would administration of about 0.4 mg of the opioid antagonist.

80. The method of claim 76 in which the opioid antagonist is selected from the group consisting of naloxone, naltrexone, and nalmefene.

81. The method of claim 76 in which the opioid antagonist comprises naloxone or a pharmaceutically acceptable salt or prodrug thereof.

82. The method of claim 76 in which the opioid antagonist comprises naltrexone or a pharmaceutically acceptable salt or prodrug thereof.

83. The method of claim 76 in which the opioid antagonist comprises nalmefene or a pharmaceutically acceptable salt or prodrug thereof.

84. The method according to claim 76 in which ingredient (a) is nalbuphine.

85. The method of claim 76 in which the pain comprises inflammatory pain.

86. The method of claim 76 in which the pain comprises neuropathic pain.

87. The method of claim 76 in which ingredient (a) and ingredient (b) are administered within eight hours of one another.

88. The method of claim 76 in which ingredient (a) and ingredient (b) are administered within two hours of one another.

89. The method of claim 76 in which ingredient (a) and ingredient (b) are administered within 15 minutes of one another.

90. The method of claim 76 in which ingredient (a) and ingredient (b) are administered together at substantially the same time.

91. The method of claim 76 comprising sequential administering of ingredient (a) and ingredient (b).

92. The method of claim 76 comprising parenteral administering of at least one of ingredient (a) and ingredient (b).

93. The method of claim 76 comprising intravenous administering of at least one of ingredient (a) and ingredient (b).

94. The method of claim 76 wherein the amount of ingredient (b) administered is 10–15-fold less than the amount of ingredient (a) administered.

95. A method of treating inflammatory pain comprising administering to a human patient in need of such treatment synergistically effective amounts of (a) nalbuphine, or a pharmaceutically acceptable salt or prodrug of nalbuphine, and (b) an opioid antagonist, a prodrug thereof, or a pharmaceutically acceptable salt thereof, wherein the opioid antagonist is selected from the group consisting of naloxone, naltrexone and nalmefene.

96. The method of claim 95 in which ingredient (b) comprises naloxone, a pharmaceutically acceptable salt thereof or a prodrug therefor.

97. The method of claim 95 wherein the amount of ingredient (b) administered is 10–15-fold less than the amount of ingredient (a) administered.

* * * * *